United States Patent
Laurence et al.

(10) Patent No.: US 7,932,497 B2
(45) Date of Patent: Apr. 26, 2011

(54) PIXELATED DETECTORS WITH DEPTH OF INTERACTION SENSITIVITY

(75) Inventors: Thomas L. Laurence, North Royalton, OH (US); Steven E. Cooke, Garfield Heights, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 902 days.

(21) Appl. No.: 11/720,761

(22) PCT Filed: Dec. 5, 2005

(86) PCT No.: PCT/IB2005/054054
§ 371 (c)(1),
(2), (4) Date: Jun. 4, 2007

(87) PCT Pub. No.: WO2006/064393
PCT Pub. Date: Jun. 22, 2006

(65) Prior Publication Data
US 2010/0127178 A1     May 27, 2010

Related U.S. Application Data

(60) Provisional application No. 60/634,567, filed on Dec. 9, 2004.

(51) Int. Cl.
*G01T 1/166* (2006.01)
(52) U.S. Cl. .................................. 250/363.04
(58) Field of Classification Search ... 250/363.01–363.1
See application file for complete search history.

(56) References Cited

U.S. PATENT DOCUMENTS

| | | | |
|---|---|---|---|
| 4,945,241 A | 7/1990 | Yamashita et al. | |
| 5,122,667 A | 6/1992 | Thompson | |
| 5,329,124 A | 7/1994 | Yamamoto et al. | |
| 5,576,546 A | 11/1996 | Gagnon | |
| 5,600,144 A | 2/1997 | Worstell | |
| 5,760,401 A * | 6/1998 | Nelleman et al. | 250/363.03 |
| 6,194,728 B1 | 2/2001 | Bosnjakovic | |
| 2003/0010924 A1 | 1/2003 | El-Hanany et al. | |
| 2003/0105397 A1 | 6/2003 | Tumer et al. | |
| 2004/0164249 A1 | 8/2004 | Crosetto | |
| 2004/0232342 A1 | 11/2004 | Aykac et al. | |

OTHER PUBLICATIONS

Orita et al., "Three-dimensional array of scintillation crystals with proper reflector arrangement for a depth of interaction detector," 2003, IEEE Nuclear Science Symposium Conference Record, vol. 4, pp. 2391-2395.*

Umehara et al., "Basic study on pulse height distribution of DOI detectors constructed of stacked crystal elements," 2003, IEEE Nuclear Science Symposium Conference Record, vol. 3, pp. 1429-1433.* Lewellen, T, K, et al.; DMice-a depth-of-interaction detector design for PET scanners; 2004; Nuclear Science Symposium Conference Record IEEE; pp. 2388-2392.

Miyaoka, R. S., et al.; Design of a Depth of Interaction (DOI) PET Detector Module; 1998; IEEE Trans. on Nuclear Science; 45(3)1069-1073.

* cited by examiner

*Primary Examiner* — David P Porta
*Assistant Examiner* — Kiho Kim (57) ABSTRACT

A radiation detector (10, 10') includes scintillator pixels (30) that each have a radiation-receiving end, a light-output end, and reflective sides extending therebetween. The reflective sides have a reflection characteristic (40, 40', 41, 44) varying between the radiation-receiving end and the light-output end such that a lateral spread of light emanating from the light-output ends of the scintillator pixels responsive to a scintillation event generated in one of the scintillator pixels depends upon a depth of the scintillation event in the scintillator pixel. A plurality of light detectors (46) optically communicate with the light-output ends of the scintillator pixels to receive light produced by scintillation events.

19 Claims, 6 Drawing Sheets

PIXELATED DETECTORS WITH DEPTH OF INTERACTION SENSITIVITY

CROSS REFERENCE TO RELATED APPLICATIONS

This application claims the benefit of U.S. provisional application Ser. No. 60/634,567 filed Dec. 9, 2004, which is incorporated herein by reference.

The following relates to the medical imaging arts. It finds particular application in positron emission tomography (PET) scanners and systems, and will be described with particular reference thereto. More generally, it finds application in medical imaging scanners and systems employing scintillation-based radiation detectors, such as computed tomography (CT) scanners and systems, nuclear imaging cameras and systems, gamma cameras, and so forth.

In positron emission tomographic imaging, a radiopharmaceutical is administered into a human or other imaging subject. Radioactive decay events occurring in the radiopharmaceutical emit positrons, which subsequently annihilate in positron-electron annihilation events each producing two oppositely directed gamma rays having energies of 511 keV. Radiation detectors surrounding the imaging subject detect the two oppositely directed gamma rays, and the detection points define a line of response therebetween. The lines of response from many positron-electron annihilation events define projection data that can be reconstructed into an image.

Resolution of the PET scanner depends upon the precision and accuracy with which the gamma ray detection events can be spatially localized. In a pixelated scintillator detector embodiment, pixelated scintillators are monitored by light detectors such as photomultiplier tubes, photodiodes, or the like. Each detection event is localized to about a single detector pixel using Anger logic or another weighted analysis of the signals of the light detectors. Because of the relatively high energy of the 511 keV gamma rays, the scintillator thickness is large, for example about two centimeters thick for some scintillator materials. This creates a large depth uncertainty in the localization of the radiation detection events, leading to reduced resolution due to parallax error in determination of the lines of response.

To provide improved depth of interaction localization, in some PET detectors a multiple-layer scintillator is used. Each scintillator layer produces light at a different wavelength, and so depth information is encoded in the wavelength of detected light. This approach substantially increases the complexity of both the scintillator and the electronics employed in processing the photomultiplier signals. Moreover, the interfaces between the different scintillator layers can produce reflection, scattering, absorption, or other optical losses. Another approach is to include a top-side photodetector in addition to the bottom side detector. The top-side photodetector signal provides an estimate of the depth of interaction. This approach also increases detector and electronics complexity. Yet another approach, disclosed in Gagnon, U.S. Pat. No. 5,576,546, estimates the depth of interaction based on the second order moments of the photodetector signals. However, the second order moments can be sensitive to noise since the position of each photodetector is squared.

The following contemplates improved apparatuses and methods that overcome the aforementioned limitations and others.

According to one aspect, a radiation detector is disclosed. Scintillator pixels each have a radiation-receiving end, a light-output end, and reflective sides extending therebetween. The reflective sides have a reflection characteristic varying between the radiation-receiving end and the light-output end such that a lateral spread of light emanating from the light-output ends of the scintillator pixels responsive to a scintillation event generated in one of the scintillator pixels depends upon a depth of the scintillation event in the scintillator pixel. A plurality of light detectors optically communicate with the light-output ends of the scintillator pixels to receive light produced by scintillation events.

According to another aspect, a radiation receiving system is disclosed, including at least one radiation detector. The radiation detector includes scintillator pixels each having a radiation-receiving end, a light-output end, and reflective sides extending therebetween, and a plurality of light detectors that optically communicate with the light-output ends of the scintillator pixels to receive light produced by scintillation events. The reflective sides of the scintillator pixels have a reflection characteristic varying between the radiation-receiving end and the light-output end such that a lateral spread of light emanating from the light-output ends of the scintillator pixels responsive to a scintillation event generated in one of the scintillator pixels depends upon a depth of the scintillation event in the scintillator pixel. A depth of interaction processor estimates a depth of interaction of a scintillation event generated in one of the scintillator pixels. The depth of interaction is estimated based on the lateral spread of light emanating from the light-output ends of the scintillator pixels responsive to the scintillation event. A signal localization processor estimates a lateral location of the scintillation event based on light received by the plurality of light detectors.

According to another aspect, a positron emission tomography (PET) scanner is disclosed. A plurality of radiation detectors surround an imaging region. Each radiation detector includes: scintillator pixels each have a radiation-receiving end, a light-output end, and reflective sides extending therebetween; and a plurality of light detectors optically communicating with the light-output ends of the scintillator pixels to receive light produced by scintillation events. The reflective sides of the scintillator pixels have a reflection characteristic varying between the radiation-receiving end and the light-output end such that a lateral spread of light emanating from the light-output ends of the scintillator pixels responsive to a scintillation event generated in one of the scintillator pixels depends upon a depth of the scintillation event in the scintillator pixel. A depth of interaction processor estimates a depth of interaction of a scintillation event generated in one of the scintillator pixels. The depth of interaction is estimated based on the lateral spread of light emanating from the light-output ends of the scintillator pixels responsive to the scintillation event. A signal localization processor estimates a lateral location of the scintillation event based on light received by the plurality of light detectors. A line of response processor determines a line of response based on two temporally coincident scintillation events. The determining of the line of response includes determining positions of the temporally coincident scintillation events based on lateral locations of the scintillation events estimated by the signal localization processor adjusted by the depths of interaction of the scintillation events estimated by the depth of interaction processor.

One advantage resides in improved image resolution.

Another advantage resides in providing improved resolution with limited additional detector and electronics complexity.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

Figure 1:
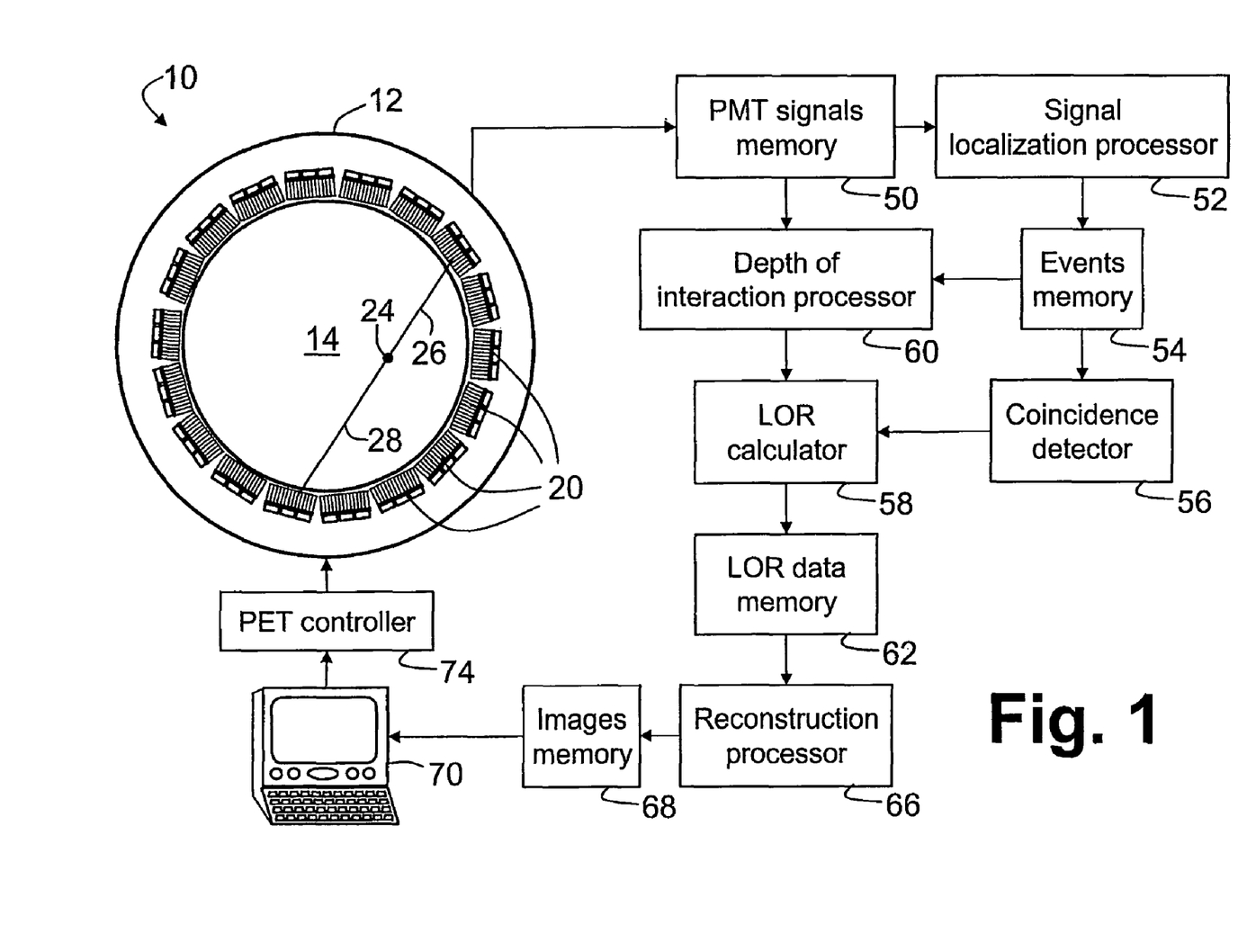
FIG. 1 diagrammatically shows a positron emission tomography (PET) system including improved depth of interaction sensitivity.

A positron emission tomography (PET) system includes a PET scanner 10 having a stationary annular gantry 12 surrounding an imaging region 14. A plurality of pixelated radiation detector modules 20 are mounted around the annular gantry with their radiation-sensitive sides facing the imaging region 14.

A human imaging subject or other type of imaging subject is placed into the imaging region 14. A radiopharmaceutical administered to the imaging subject produces nuclear decay events that emit as one of the products a positron. This positron rapidly annihilates with a nearby electron, producing a pair of oppositely directed 511 keV gamma rays. As an illustration, in FIG. 1 an example nuclear decay event 24 is diagrammatically indicated, with the paths of the two oppositely directed gamma rays indicated by lines 26, 28 extending away in opposite directions from the nuclear decay event 24. Each gamma ray strikes one of the pixelated radiation detector modules 20.

Figure 2:
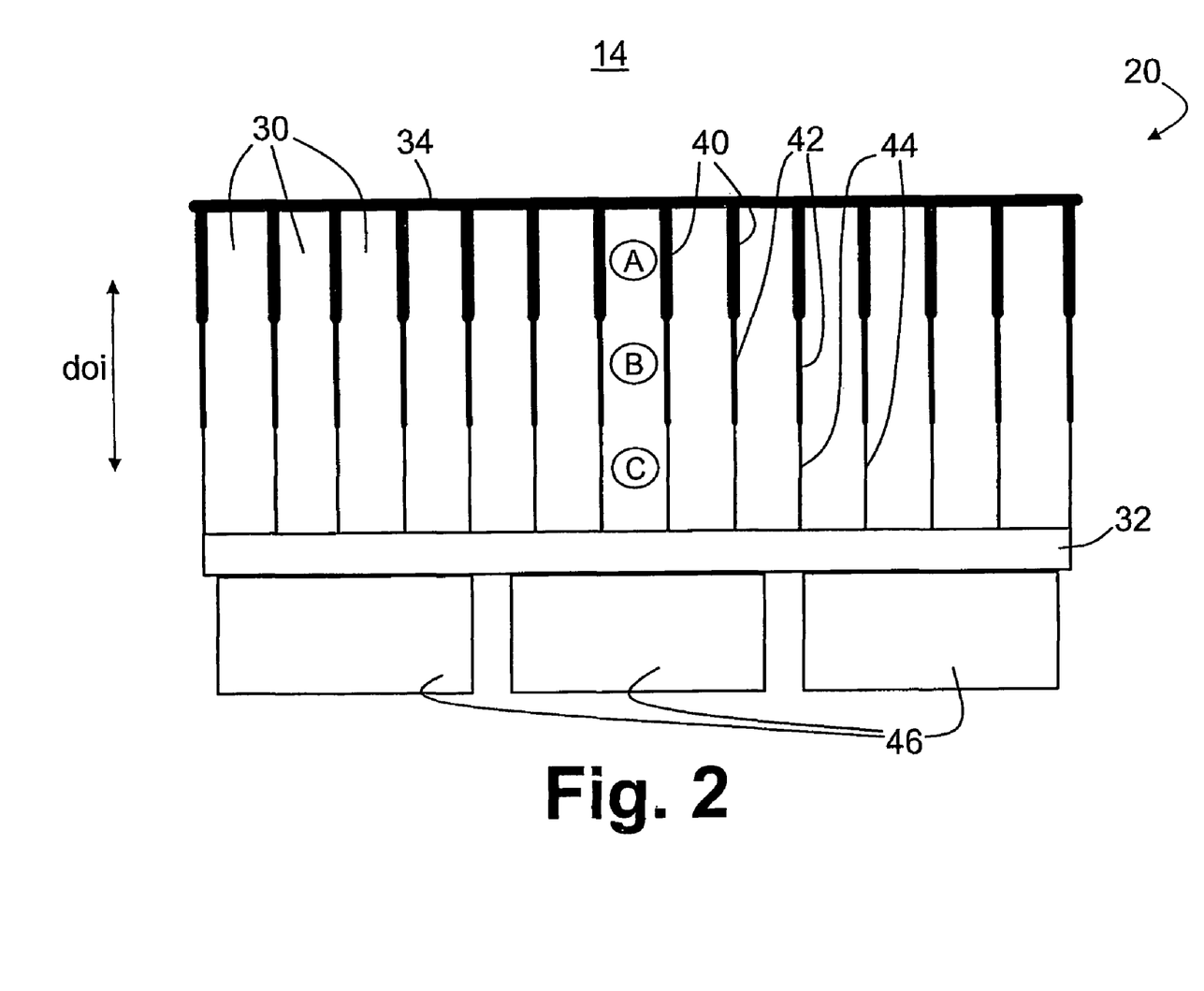
FIG. 2 diagrammatically shows a side sectional view of one of the radiation detector modules of the PET scanner of FIG. 1. Scintillation events at three example depths of interaction are indicated by the labels "A", "B", and "C".

With continuing reference to FIG. 1 and with further reference to FIG. 2, each pixelated radiation detector module 20 includes a an array of scintillator pixels 30 each made of a radiation-sensitive material such as Ce-doped $Gd_2SiO_5$ (GSO), Ce-doped $Lu_2SiO_5$ (LSO), or so forth. In order to provide sufficient gamma ray stopping power, the scintillator pixels 30 are extended in a depth of interaction direction (denoted "doi" in FIG. 2), and are packed together in the two-dimensional plane transverse to the depth of interaction direction. In some embodiments, the each scintillator pixel is a crystal of GSO about 2 cm along the depth of interaction direction and about 0.2-0.4 $cm^2$ in cross-sectional area transverse to the depth of interaction direction; however, other scintillator pixel materials and dimensions can be used, with selection preferably based on the type and energy of the radiation to be detected, the geometry of the gantry, the desired resolution, sensitivity considerations, and so forth.

A gamma ray striking one of the scintillator pixels 30 generates a scintillation event that emits a flash of light. Some of the scintillation light is directed generally away from the imaging region 14, exits a light output end of the scintillator pixel 30, and enters into a back-side planar light pipe 32 disposed at the output ends of the scintillator pixels 30. Some of the scintillation light is directed toward the imaging region 14; however, this light impinges upon a front-side reflector 34 disposed at the radiation-receiving ends of the scintillator pixels 30 and reflects generally backward toward the backside light pipe 32. The front-side reflector 34 is selected to be substantially transparent to the radiation being detected (for example, the 511 keV gamma rays in the case of a PET scanner) but highly reflective (ideally, close to 100% reflective) for the light produced by a scintillation event.

The reflector 34 can be, for example, a thin reflective film or coating disposed over the radiation-receiving ends of the scintillator pixels 30.

The sides of the pixels 30 are also reflective, but with a reflection/transmission characteristic that varies between the radiation-receiving end and the light-output end of the scintillator pixel 30. In the pixelated detector module 20, each reflective side has a plurality of reflective regions 40, 42, 44 distributed between the radiation-receiving end and the light-output end of the scintillator pixel 30. Each of the regions 40, 42, 44 has substantially uniform reflectivity, and the reflectivity of the sides changes at the junction of two reflective regions. The reflective region 40 is disposed closest to the radiation-receiving end of the scintillator pixel 30 and has the highest reflectivity of the three reflective regions 40, 42, 44. In some embodiments, the reflective region 40 has substantially the same reflectivity as the front-side reflector 34. The reflective region 44 is disposed closest to the light-output end of the scintillator pixel 30 and has the lowest reflectivity of the three reflective regions 40, 42, 44. In some embodiments, the region 40 has a reflectivity of 100%, the region 42 has a reflectivity of 75%, and the region 44 has a reflectivity of 50%; however, other reflectivity values can be used.

In FIG. 2, the differences in reflectivity of the reflective regions 40, 42, 44 are diagrammatically indicated by using a thicker line thickness to indicate higher reflectivity. In some embodiments, the reflective regions 40, 42, 44 are pieces of reflective paper disposed between the scintillator pixels 30, in which the reflective paper used for the regions 40 has higher reflectivity than the reflective paper used for the regions 42, and the reflective paper used for the regions 42 has higher reflectivity than the reflective paper used for the regions 44. Instead of reflective paper, a reflective metal foil or other reflective planar element can be inserted between scintillator pixels 30. In other embodiments, reflective coatings are applied to the sides of the scintillator pixels 30 prior to assembly of the pixelated detector module 20, again with coatings of appropriate reflectivity used for each of the reflective regions 40, 42, 44. In yet other embodiments, a differential roughening is formed on the sides of each scintillator pixel 30, and then a reflective paper, coating, or the like having substantially uniform reflectivity is disposed along the entire side. In these embodiments, the differential roughening provides the varying reflection characteristic. For example, the surfaces of the portions of the sides corresponding to region 40 may be left smooth, while the surfaces of the portions of the sides corresponding to regions 42, 44 may be made increasingly rough so as to increase light scattering and/or transmission through the regions 42, 44 to reduce the effective reflectivity of the regions 42, 44.

The front-side reflector 34 along with the reflective regions 40, 42, 44 have the general effect of channeling light to the back-side planar light pipe 32 disposed at the output ends of the scintillator pixels 30. A plurality of light detectors, such as illustrated photomultiplier tubes (PMT's) 46, photodiodes, or the like, are disposed below the back-side planar light pipe 32 and optically communicate with the light-output ends of the scintillator pixels 30 via the light pipe 32 to receive light produced by scintillation events. The back-side planar light pipe 32 provides light distribution and refractive index matching to improve optical coupling between the light-output ends of the scintillator pixels 30 and the PMT's 46. The PMT's 46 or other light detectors are generally larger in area than the scintillator pixels 30. Moreover, because of light spreading in the light pipe 32 and partial light transmission of the partially reflective sides of the scintillator pixels 30, light from a single scintillation event generally spreads out laterally (that is, transverse to the depth of interaction direction ("doi")) such that more than one PMT 46 receives light from a single scintillation event.

With returning reference to FIG. 1, a PMT signals memory 50 collects and stores the signals from the PMT's 46. Scintillation events are localized by a signal localization processor 52. In some embodiments, the signal localization processor 52 identifies the lateral position of the scintillation event based on the lateral position of the PMTs that generates the largest signal responsive to the scintillation event. However, as seen in FIG. 2, the lateral area of the PMT's 46 is typically substantially larger than the lateral area of the scintillator pixels 30. Accordingly, in some embodiments the signal localization processor 52 employs an Anger logic or other lateral localization algorithm to more precisely laterally localize the scintillation event. Indexing the PMT's 46 that receive light from the scintillation event as $T_i$ and assigning position values $p_i$ for each PMT $T_1$ respective to the position of the "high tube" PMT that generates the strongest signal responsive to the scintillation event, Anger logic suitably laterally localizes the scintillation event according to:

$$p(\text{event}) = \frac{\sum_i p_i \cdot \int S(T_i) \cdot dt}{\sum_i \int S(T_i) \cdot dt}, \quad (1)$$

where $S(T_i)$ is the signal of tube $T_i$ as a function of time, the integrals are the time-integrated signal produced by each tube, and p(event) is the lateral position of the scintillation event. It should be appreciated that the term "lateral position" relates to the position of the scintillation event in the plane transverse to the depth of interaction direction ("doi") which is itself referenced to the local coordinate system of the particular pixelated radiation detector module 20 that receives the scintillation event. For the illustrated geometry in which the scintillator pixels 30 have lateral areas much smaller than the lateral areas of the PMT's 46, the lateral position substantially identifies in which one of the scintillator pixels 30 the scintillation event occurred.

The localized scintillation event is stored in an events memory 54. For PET imaging, a radiation event of interest is one in which both oppositely directed gamma rays of a positron-electron annihilation event are detected, such that a line of response ("LOR") can be determined. Accordingly, a coincidence detector 56 monitors the events stored in the events memory 54 to detect two substantially simultaneous scintillation events corresponding to the gamma rays produced by a positron-electron annihilation event. Typically, the coincidence detector 56 employs a temporal coincidence window, such that any two scintillation events lying within the temporal coincidence window are taken to be "substantially simultaneous." Additionally, the coincidence detector 56 optionally takes into account other information in determining whether a pair of scintillation events is of interest. For example, the coincidence detector 56 can take into account that the gamma rays produced by a positron-electron annihilation event have energies of 511 keV. A total energy of the scintillation event is suitably represented by:

$$E = \sum_i \int S(T_i) \cdot dt, \quad (2)$$

where E represents the total energy produced by the scintillation event. By limiting events of interest to those scintillation events whose total energy value E lies within an energy window corresponding to 511 keV, improved selectivity is obtained.

When the coincidence detector 56 identifies a coincident pair of scintillation events, a line or response ("LOR") calculator 58 determines a line or response connecting the two scintillation events. To reduce parallax error in computing the LOR, a depth of interaction processor 60 determines a depth of the scintillation event in the depth of interaction direction ("doi"). The depth of interaction processor 60 estimates the depth based on a depth-dependent lateral spread of light emanating from the light-output ends of the scintillator pixels 30 responsive to the scintillation event. The depth-dependent lateral spread is a consequence of the reflective sides having the varying reflection characteristic between the radiation-receiving end and the light-output end.

The resultant LOR is stored in a LOR data memory 62. A reconstruction processor 66 reconstructs the LOR data into a reconstructed image of at least a portion of the imaging subject disposed in the imaging region 14. The LOR data substantially corresponds to projection data, and the reconstruction processor 66 can use any suitable reconstruction algorithm, such as a filtered backprojection algorithm. The reconstructed image is stored in an images memory 68, and can be displayed on a computer 70 or other user interface, stored in a non-volatile memory, printed by a printer, transmitted via a local area network or the Internet, or otherwise utilized. In some embodiments, the computer 70 also provides user interfacing with a PET controller 74 through which the user can control the PET scanner 10.

Figure 3:
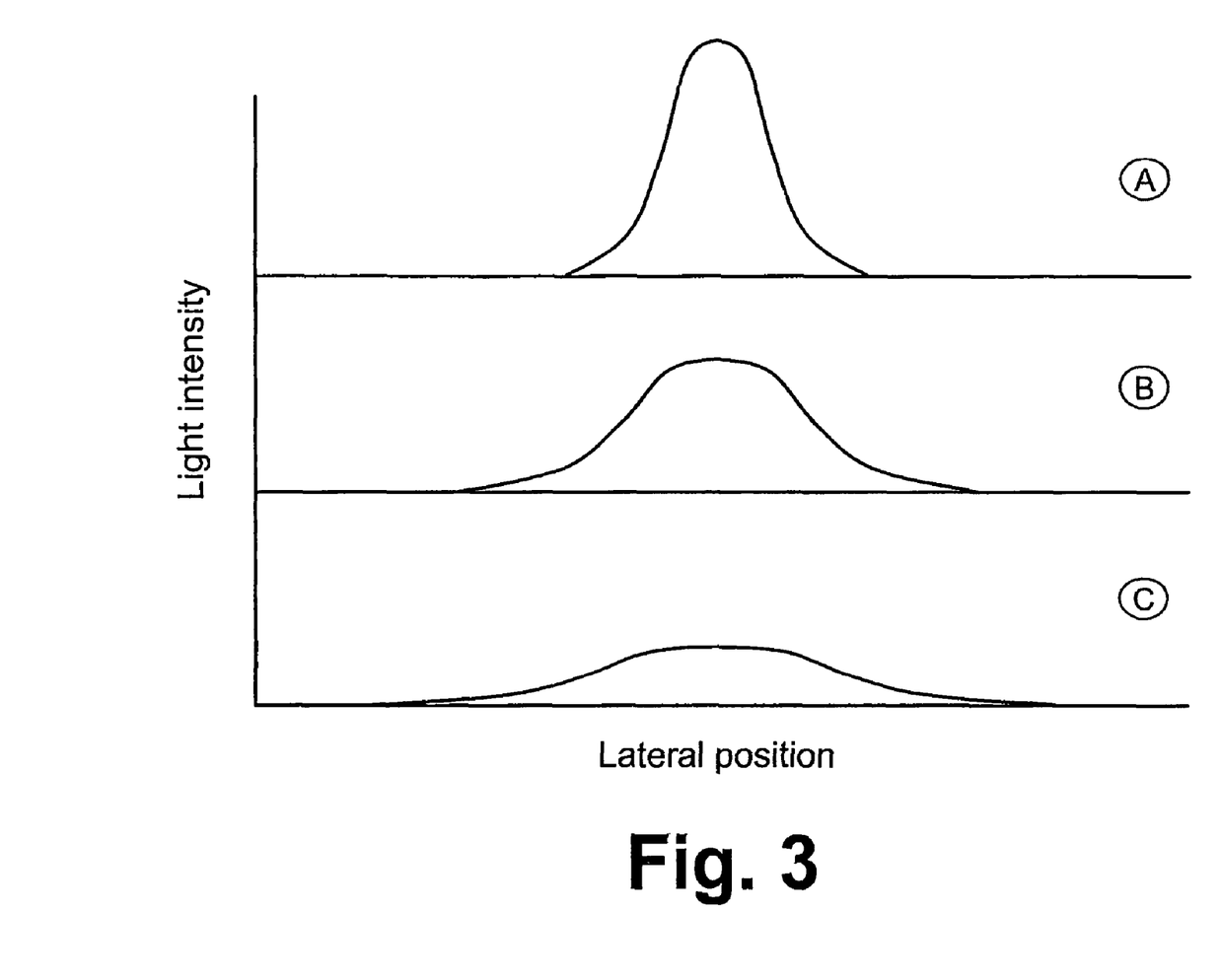
FIG. 3 plots light intensity versus lateral position for the scintillation events at the three different depths of interaction "A", "B", and "C" of FIG. 2.
Figure 4:
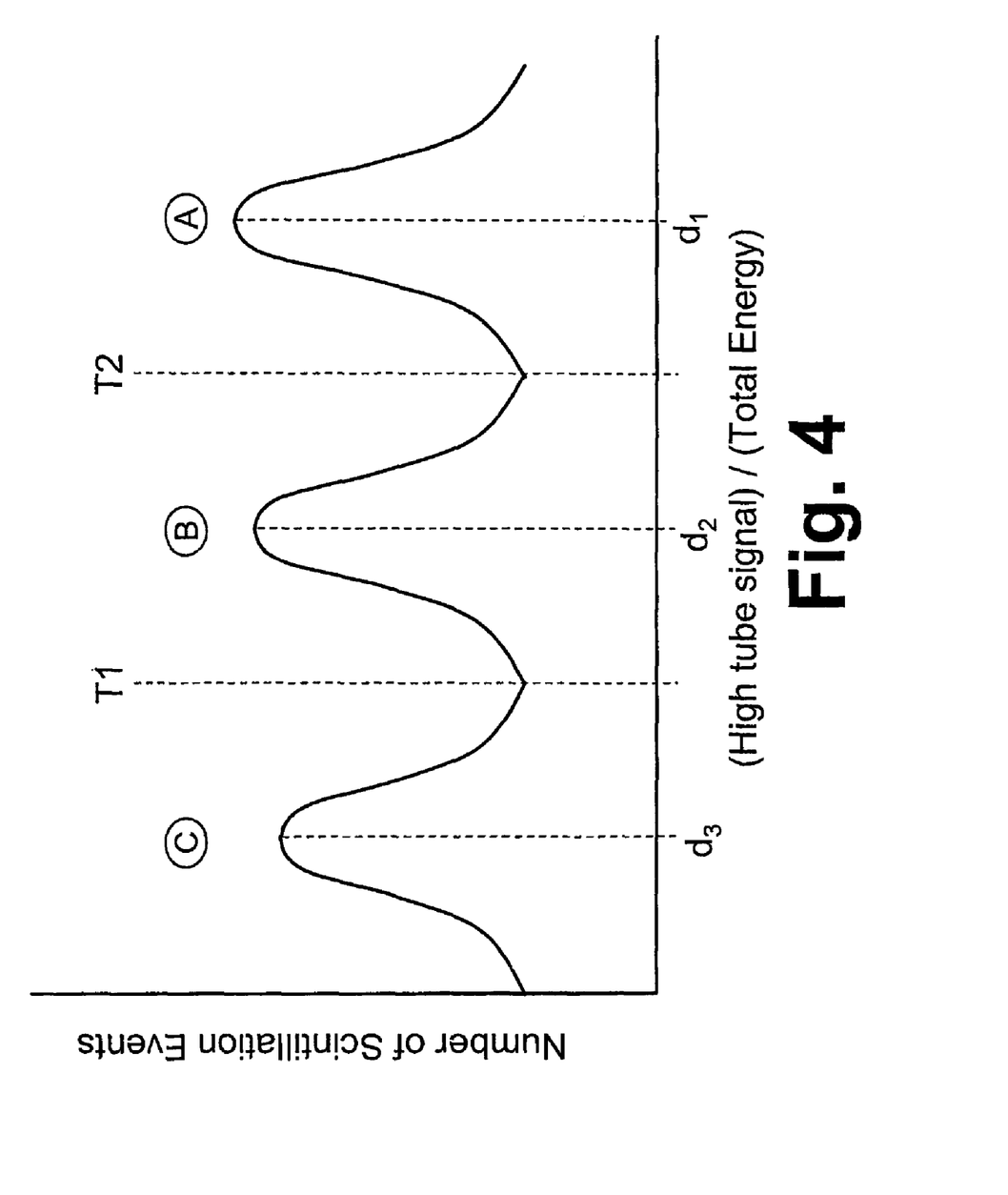
FIG. 4 plots a histogram of scintillation event counts versus the integrated high tube signal normalized by an energy sum for the radiation detector module of FIG. 2.

With reference to FIGS. 2-4, some suitable embodiments of the depth of interaction processor 60 are described. As examples, scintillation events labeled "A", "B", and "C" in FIG. 2 are illustrated. The scintillation event "A" occurs within the region of the scintillator pixel 30 surrounded by the highly reflective regions 40. The scintillation event "B" occurs within the region of the scintillator pixel 30 surrounded by the intermediately reflective regions 42. The scintillation event "C" occurs within the region of the scintillator pixel 30 surrounded by the least reflective regions 44.

FIG. 3 plots the light intensity spreading at the PMT's 46 as a function of lateral position for each of the scintillation events labeled "A", "B", and "C" in FIG. 2. The scintillation event "A" has a narrow light intensity spread at the PMT's 46 because the highly reflective regions 40 together with the nearby highly front-side reflector 34 tend to focus the light relatively tightly toward the back-side planar light pipe 32. In contrast, the scintillation event "C" has a relatively broader light intensity spread at the PMT's 46 because the least reflective regions 44 allow a substantial portion of the light to transmit through to nearby scintillator pixels 30. The scintillation event "B" has an intermediate light intensity spread at the PMT's 46 due to the intermediate reflectivity of the reflective regions 42. Accordingly, by quantifying the light spread, the depth of interaction is suitably estimated.

The light spread can be quantified in various ways. One approach is to normalize the integrated high tube signal by the total energy of Equation (2), giving a light spread metric of $$m(\text{spread}) = \frac{\int S(T_{high}) \cdot dt}{\sum_i \int S(T_i) \cdot dt}, \quad (3)$$

where $T_{high}$ denotes the PMT generating the highest signal for a given scintillation event, and m(spread) is a measure of the light spread.

With reference to FIG. 4, the three regions 40, 42, 44 each having substantially uniform reflectivity results in three signal spread "modes" corresponding to the three regions 40, 42, 44. FIG. 4 plots a histogram of the number of scintillation events as a function of the light spread metric m(spread). The histogram of FIG. 4 can be computed by light ray tracing or other computational techniques, or can be measured experimentally for the pixelated radiation detector module 20.

In some embodiments, the presence of these light spread modes is used to define thresholds, such as the example thresholds "T1" and "T2" illustrated in FIG. 4, for binning the depth of interaction into one of three discrete bins corresponding to the three regions 40, 42, 44. Thus, any scintillation event having m(spread)>T2 is assigned the depth of interaction position $d_1$; any scintillation event having T1<m(spread)<T2 is assigned the depth of interaction position $d_2$; and any scintillation event having m(spread)<T1 is assigned the depth of interaction position $d_3$.

Figure 5:
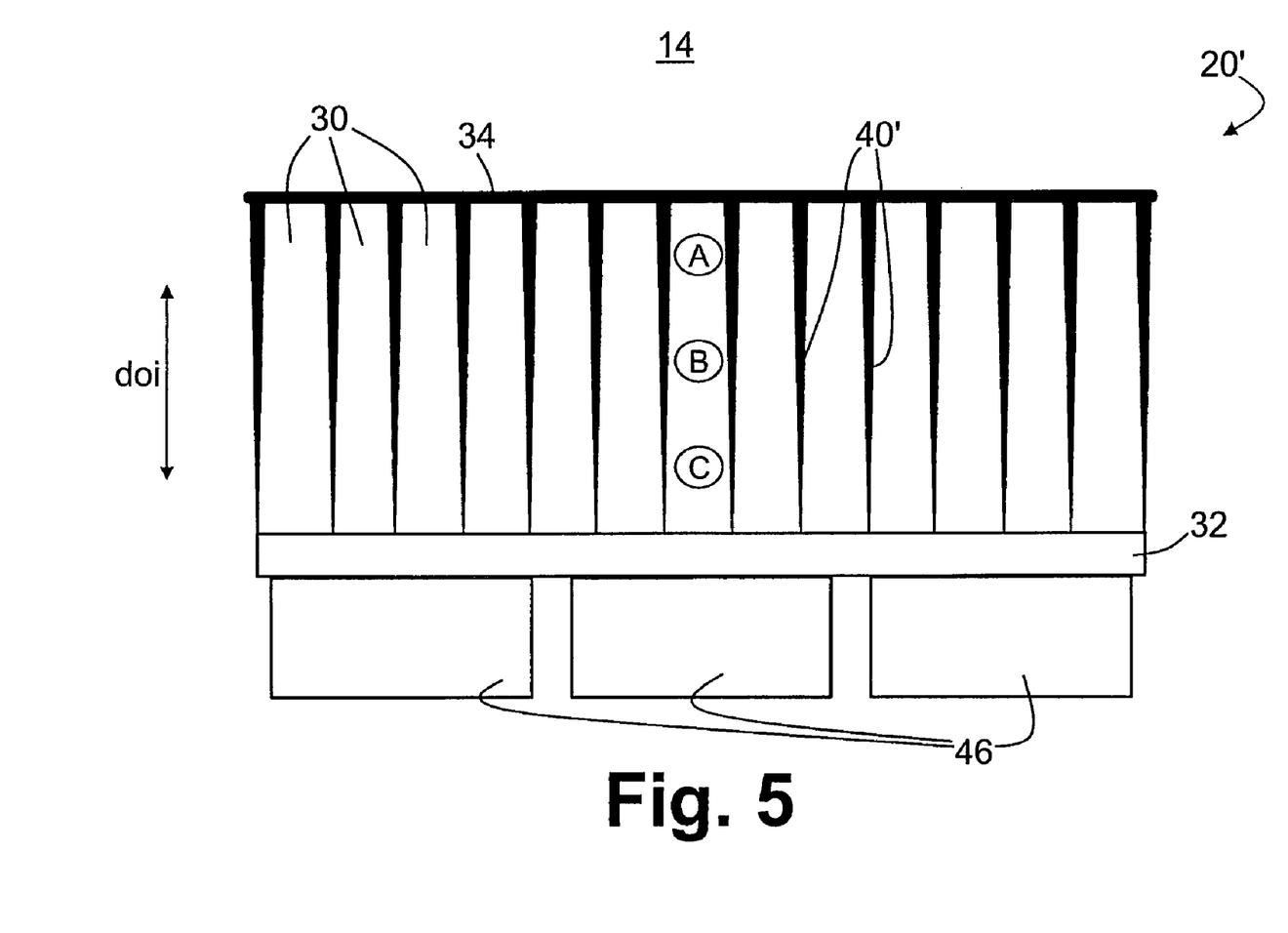
FIG. 5 diagrammatically shows a side sectional view of another radiation detector module suitable for use in the PET scanner of FIG. 1. Scintillation events at three example depths of interaction are indicated by the labels "A", "B", and "C".

With reference to FIG. 5, another pixelated radiation detector 20' is illustrated that can suitably be used in place of the pixelated radiation detector 20 in the PET scanner 10 of FIG. 1. The pixelated radiation detector 20' includes the scintillator pixels 30, back-side planar light pipe 32, front-side reflector 34, and PMT's 46 of the pixelated radiation detector 20. The pixelated radiation detector 20' differs from the pixelated radiation detector 20 in that in the detector 20' the sides of the scintillator pixels 30 have a single continuously varying reflective region 40' having a reflectivity that varies continuously between the radiation-receiving end and the light-output end. The continuously varying reflective region 40' has a highest reflectivity proximate the radiation-receiving end and a lowest reflectivity proximate the light-output end. In some embodiments, the reflectivity of the reflective region 40' is close to 100% at the radiation-receiving end and decreases in a linear fashion to a reflectivity of 50% at the light-output end. These are example values, and other reflectivity values can be used. Moreover, the gradual change in reflectivity can be other than linear, for example quadratic. In FIG. 5, the gradual decrease in reflectivity of the reflective region 40' is diagrammatically indicated by using a gradually thinning line thickness to indicate the gradually decreasing reflectivity.

As with the pixelated radiation detector 20, the light spread of the scintillation events labeled "A", "B", and "C" in FIG. 5 increases with increasing depth of interaction due to increased light transmission through the sides of the scintillator pixels 30 at deeper depths of interaction. Accordingly, a suitable light spread metric such as the example light spread metric of Equation 3 can be used in conjunction with the pixelated radiation detector 20' to estimate the depth of interaction.

Figure 6:
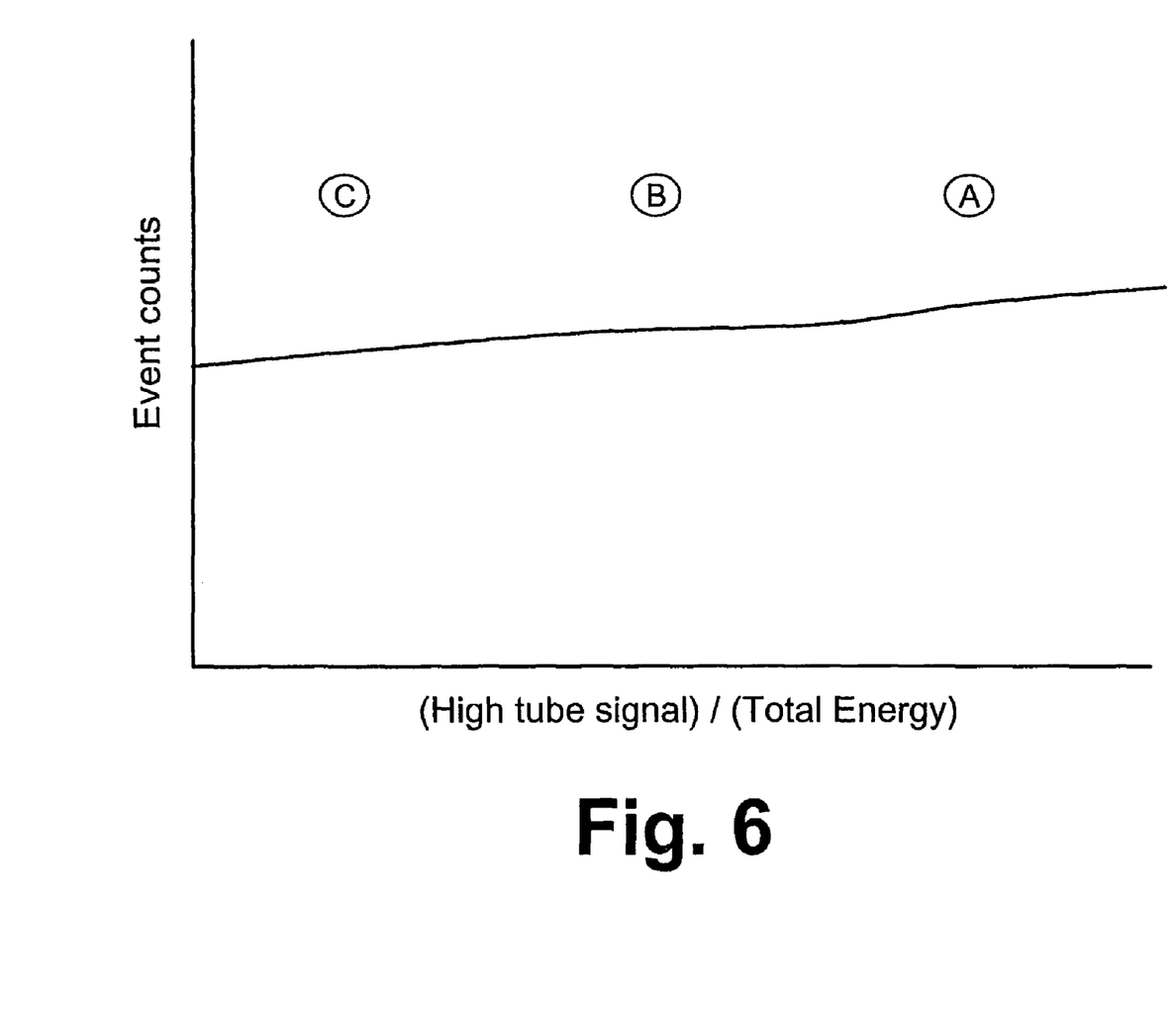
FIG. 6 plots a histogram of scintillation event counts versus the integrated high tube signal normalized by an energy sum for the radiation detector module of FIG. 5.

FIG. 6 plots a histogram of the number of scintillation events as a function of the light spread metric m(spread) of Equation (3) for the radiation detector 20'. Unlike the histogram for the radiation detector 20 shown in FIG. 4, the histogram of FIG. 6 for the radiation detector 20' does not exhibit well-defined modes, because the reflectivity of the sides of the scintillator pixels 30 vary continuously in the radiation detector 20', rather than in discrete steps as in the radiation detector 20.

Other light spread metrics can be used in place of Equation (3). For example, the depth of interaction computation method employing second moment computations disclosed in Gagnon, U.S. Pat. No. 5,576,546, is readily adapted for use with the pixelated radiation detector module 20 of FIG. 2, or with the pixelated radiation detector module 20' of FIG. 5. The varying reflectivity of the sides of the scintillator pixels 30 provided by the reflective regions 40, 42, 44 of the detector module 20, or provided by the continuously varying reflectivity region 40' of the detector module 20', substantially improves the precision and accuracy of the depth of interaction computation method of Gagnon '546, because it causes the second moments to vary strongly with the depth of interaction.

The illustrated PET embodiment is an example. The depth of interaction estimation apparatuses and methods described herein are suitably employed in other types of radiation detectors and other imaging modalities, such as in single photon emission computed tomography (SPECT), transmission computed tomography (CT), and the like. Moreover, the illustrated reflective sides 40, 40', 42, 44, are examples, and other configurations of varying reflectivity along the sides of the scintillator pixels 30 can be used. For example, two regions, or more than three regions, of substantially uniform reflectivity can be used in place of the illustrated three regions 40, 42, 44. Further, it is to be appreciated that the light produced by scintillation events can be visible light, infrared light, or ultraviolet light.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A radiation detector comprising:
    scintillator pixels each having a radiation-receiving end, a light-output end, and reflective sides extending therebetween, the reflective sides having a reflection characteristic varying between the radiation-receiving end and the light-output end such that a lateral spread of light emanating from the light-output ends of the scintillator pixels responsive to a scintillation event generated in one of the scintillator pixels depends upon a depth of the scintillation event in the scintillator pixel, wherein each reflective side has a reflectivity distributed between the radiation-receiving end and the light-output end, the reflectivity nearest the radiation-receiving end having the highest reflectivity; and
    a plurality of light detectors optically communicating with the light-output ends of the scintillator pixels to receive light produced by scintillation events.

2. The radiation detector as set forth in claim 1, wherein each reflective side has a plurality of regions each having uniform reflectivity distributed between the radiation-receiving end and the light-output end.

3. The radiation detector as set forth in claim 2, wherein each reflective side has three regions distributed between a most reflective region adjacent the radiation-receiving end and a least reflective region adjacent the light-output end.

4. The radiation detector as set forth in claim 1, further including:
a reflective surface disposed on top of the radiation-receiving ends of the scintillator pixels.

5. The radiation detector as set forth in claim 1, wherein the reflection characteristic further includes a lowest reflectivity proximate the light-output end, and a monotonically non-increasing reflectivity between the radiation-receiving end and the light-output end.

6. The radiation detector as set forth in claim 5, wherein the monotonically non-increasing reflectivity between the radiation-receiving end and the light-output end includes two or more regions of substantially uniform reflectivity.

7. The radiation detector as set forth in claim 5, wherein the monotonically non-increasing reflectivity between the radiation-receiving end and the light-output end includes a region of continuously decreasing reflectivity between the radiation-receiving end and the light-output end.

8. The radiation detector as set forth in claim 1, wherein the sides include one or more reflective materials disposed thereon defining the varying reflection characteristic between the radiation-receiving end and the light-output end.

9. The radiation detector as set forth in claim 1, wherein the sides include one or more reflective coatings disposed thereon defining the varying reflection characteristic between the radiation-receiving end and the light-output end.

10. A positron emission tomography (PET) scanner comprising:
a plurality of radiation detectors as set forth in claim 1 surrounding an imaging region;
a depth of interaction processor that estimates a depth of interaction of a scintillation event generated in one of the scintillator pixels, the depth of interaction being estimated based on the lateral spread of light emanating from the light-output ends of the scintillator pixels responsive to the scintillation event;
a signal localization processor that estimates a lateral location of the scintillation event based on light received by the plurality of light detectors; and
a line of response processor that determines a line of response based on two temporally coincident scintillation events, the determining of the line of response including determining positions of the temporally coincident scintillation events based on lateral locations of the scintillation events estimated by the signal localization processor adjusted by the depths of interaction of the scintillation events estimated by the depth of interaction processor.

11. A radiation detector comprising:
scintillator pixels each having a radiation-receiving end, a light-output end, and reflective sides extending therebetween, the reflective sides having a reflection characteristic varying between the radiation-receiving end and the light-output end such that a lateral spread of light emanating from the light-output ends of the scintillator pixels responsive to a scintillation event generated in one of the scintillator pixels depends upon a depth of the scintillation event in the scintillator pixel, wherein the sides include a texturing producing the varying reflection characteristic between the radiation-receiving end and the light-output end; and
a plurality of light detectors optically communicating with the light-output ends of the scintillator pixels to receive light produced by scintillation events.

12. A radiation receiving system comprising:
at least one radiation detector including:
scintillator pixels each having a radiation-receiving end, a light-output end, and reflective sides extending therebetween, the reflective sides having a reflection characteristic varying between the radiation-receiving end and the light-output end such that a lateral spread of light emanating from the light-output ends of the scintillator pixels responsive to a scintillation event generated in one of the scintillator pixels depends upon a depth of the scintillation event in the scintillator pixel, wherein each reflective side has a plurality of regions each having uniform reflectivity distributed between the radiation-receiving end and the light-output end, and
a plurality of light detectors optically communicating with the light-output ends of the scintillator pixels to receive light produced by scintillation events;
a depth of interaction processor that estimates a depth of interaction of a scintillation event generated in one of the scintillator pixels, the depth of interaction being estimated based on the lateral spread of light emanating from the light-output ends of the scintillator pixels responsive to the scintillation event, wherein the depth of interaction processor estimates the depth of interaction by one of:
estimating the depth of interaction as corresponding to an average depth of a selected one of the plurality of regions based on the lateral spread of light corresponding to a spreading mode associated with the selected region, and
thresholding a quantitative measure of the lateral spread of light; and
a signal localization processor that estimates a lateral location of the scintillation event based on light received by the plurality of light detectors.

13. The radiation receiving system as set forth in claim 12, wherein the signal localization processor employs an Anger logic.

14. The radiation receiving system as set forth in claim 12, wherein the depth of interaction processor estimates a depth of interaction as corresponding to an average depth of a selected one of the plurality of regions based on the lateral spread of light corresponding to a spreading mode associated with the selected region.

15. The radiation receiving system as set forth in claim 12, wherein the depth of interaction processor estimates the depth of interaction by thresholding a quantitative measure of the lateral spread of light.

16. A radiation receiving system comprising:
at least one radiation detector including:
scintillator pixels each having a radiation-receiving end, a light-output end, and reflective sides extending therebetween, the reflective sides having a reflection characteristic varying between the radiation-receiving end and the light-output end such that a lateral spread of light emanating from the light-output ends of the scintillator pixels responsive to a scintillation event generated in one of the scintillator pixels depends upon a depth of the scintillation event in the scintillator pixel, and
a plurality of light detectors optically communicating with the light-output ends of the scintillator pixels to receive light produced by scintillation events;
a depth of interaction processor that estimates a depth of interaction of a scintillation event generated in one of the scintillator pixels, the depth of interaction being estimated based on the lateral spread of light emanating from the light-output ends of the scintillator pixels responsive to the scintillation event wherein the depth of interaction processor estimates the depth of interaction based on a ratio of a strongest integrated signal produced by any of the light detectors responsive to the scintillation event divided by a combined value of integrated signals produced by the plurality of light detectors responsive to the scintillation event; and a signal localization processor that estimates a lateral location of the scintillation event based on light received by the plurality of light detectors.

17. The radiation receiving system as set forth in claim 16, wherein said combined value of signals is the integrated signal summed over the light detectors detecting the scintillation event.

18. The radiation receiving system as set forth in claim 16, wherein the depth of interaction processor estimates the depth of interaction using:

$$m(\text{spread}) = \frac{\int S(T_{high}) \cdot dt}{\sum_i \int S(T_i) \cdot dt}$$

where i indexes light detectors that generate a signal responsive to the scintillation event, $S(T_i)$ denotes the signal from the light detector $T_i$ as a function of time, $S(T_{high})$ denotes the signal from that light detector $T_{high}$ generating the highest signal for a given scintillation event as a function of time, and m(spread) is a measure of the light spread.

19. The radiation receiving system as set forth in claim 16, wherein the signal localization processor employs an Anger logic.

* * * * *